United States Patent [19]

Puthawala et al.

[11] Patent Number: 4,897,076
[45] Date of Patent: Jan. 30, 1990

[54] DETACHABLE AND REMOTE CONTROLLABLE AFTERLOADING DEVICE FOR RADIATION

[76] Inventors: Ajmel A. Puthawala, 11859 Cresta Verde Dr., Whittier, Calif. 90601; Anwer A. Puthawala, 46 Weiselstrasse, Erlangen Buckenhof, Fed. Rep. of Germany, 8520

[21] Appl. No.: 802,264

[22] Filed: Nov. 25, 1985

[30] Foreign Application Priority Data

Nov. 23, 1984 [DE] Fed. Rep. of Germany ..... 34427627

[51] Int. Cl.⁴ .................. G21F 5/02; A61N 5/01; A61M 37/04
[52] U.S. Cl. ........................... 600/7; 600/3; 600/8; 250/497.1
[58] Field of Search ................ 128/1.1, 1.2; 250/497.1; 198/690.1; 209/904, 907; 600/3, 6-8, 1

[56] References Cited

U.S. PATENT DOCUMENTS

| | | | |
|---|---|---|---|
| 1,442,051 | 1/1923 | Cummings | 128/1.2 |
| 1,494,826 | 5/1924 | Viol | 128/1.2 |
| 3,393,317 | 7/1968 | Spencer | 250/160 |
| 3,669,093 | 6/1972 | Sanerwein et al. | 128/1.1 |
| 3,861,380 | 1/1975 | Chassagne et al. | 128/1.2 |
| 4,150,298 | 4/1979 | Brault et al. | 250/497.1 |
| 4,211,928 | 7/1980 | Parsons et al. | 250/497.1 |
| 4,225,790 | 9/1980 | Parsons et al. | 250/497.1 |
| 4,233,517 | 11/1980 | Van't Hooft | 128/1.1 |
| 4,281,252 | 7/1981 | Parsons et al. | 250/497.1 |
| 4,314,157 | 2/1982 | Gaines | 250/497.1 |
| 4,508,119 | 4/1985 | Tukamoto | 128/1.1 |
| 4,627,420 | 12/1986 | Katz | 128/1.1 |
| 4,631,415 | 12/1986 | Sanerwein et al. | 250/497.1 |
| 4,692,628 | 9/1987 | Sanerwein et al. | 250/497.1 |

FOREIGN PATENT DOCUMENTS

| | | | |
|---|---|---|---|
| 0037678 | 10/1981 | European Pat. Off. | |
| 0064860 | 11/1982 | European Pat. Off. | |
| 0152124 | 8/1985 | European Pat. Off. | 128/1.2 |

Primary Examiner—Max Hindenburg
Assistant Examiner—John C. Hanley
Attorney, Agent, or Firm—Sheldon & Mak; Denton L. Anderson

[57] ABSTRACT

An afterloading device for handling radioactive material used in connection with the irradiation of malignant tumors has (1) a radiation-shielded container, (2) a number of channels within the container for transporting radioactive material-containing ribbons to and from the radiation therapy patient, (3) a device for propelling such ribbons along the channels and into external tubes leading into the patient, and (4) a coupling element connecting the channels to the external tubes leading into the patient, which coupling element is detachable from the container, channels, and propelling device. The propelling device is preferably ring magnets movable along the exterior of the channels. The coupling element can be made up of three perforated plates arranged in parallel: a fixed first outside plate at whose perforations are attached the channels; a second fixed outside plate at whose perforations are attached the external tubes; and a slideable center plate adapted to clamp ribbons located between the two fixed outside plates. Each ribbon has a substantially elongated body containing radioactive material and a non-radioactive ferromagnetic material.

12 Claims, 4 Drawing Sheets

DETACHABLE AND REMOTE CONTROLLABLE AFTERLOADING DEVICE FOR RADIATION

BACKGROUND

The present invention is directed to a device for handling radioactive material used in connection with the irradiation of malignant tumors (radiation therapy).

Radiation therapy is a common and accepted procedure for treatment of malignant tumors. A particular variant of radiation therapy, brachytherapy, is used for both interstitial and intercavitary applications. In brachyrnerapy, thin, hollow conduits (catheter tubes and/or steel needles) are initially placed at precise locations within or adjacent to the tumor, such that the ends of the conduits are accessible outside the patient's body. Thereafter, small, precisely measured quantities of radioactive material (most commonly radioactive isotopes of iridium, iodine or cesium) are placed within the conduits (commonly termed, "afterloading") and maintained in place for a selected period of time. When the therapy session is completed, the radioactive material is withdrawn from the conduits and placed in waste storage for future disposal. The number of radioactivity-loaded conduits varies with each case depending on various factors such as the size of the tumor and its location, but it is frequently as many as 10 or 30 and is sometimes greater than 50.

The small quantities of radioactive material are generally afterloaded into the pre-placed conduits by placing the radioactive material within the forward end of flexible tubes and then pushing the tubes into the conduits. The flexible tubes are commonly made of low friction material such as a plastic. The radioactive material is commonly placed at the forward end of the tube in several, discrete quantities, called "seeds." The seed-containing flexible tubes are commonly termed "ribbons."

Afterloading ribbons into a patient and removing the ribbons from the patient are procedures which require caution so as not to expose therapy personnel to repeated dosages of radiation. Historically, therapy personnel have afterloaded and removed the ribbons manually, using long, forceps-like tools and working around lead shields to minimize their radiation exposure. By this manual procedure, ribbons are removed from their radiation-insulated storage containers and placed, one at a time, into the interstitial or intercavitary conduits. Later, after the therapy session is complete, therapy personnel reverse the procedure, removing the ribbons from the conduits one at a time and placing them in a radiation-insulated storage container for future disposal. The procedures are obviously awkward, time consuming and, to an extent, dangerous to therapy personnel.

Devices for automatically handling the ribbons by mechanical, non-manual means are known in the art. However, these devices are limited in their utility by the fact that they cannot be disconnected from the ribbons during the therapy sessions. Consequently, the patient remains "attached" to the device, an obvious inconvenience to the patient. Furthermore, the device is "tied up" with the therapy of a single patient, an equally obvious economic problem of significant proportions to the medical institution providing the therapy. Consequently, the practical applicability of the automatic ribbon-handling devices of the prior art have been restricted almost exclusively to snort (usually, high-dosage) therapy sessions of less than an hour or so. Longer therapy sessions continue to require the time-consuming and dangerous manual handling of the ribbons during afterloading and subsequent removal.

In view of these problems associated with the existing ribbon-handling techniques and devices, there is a need for a device which can afterload radiation-containing ribbons into a radiation therapy patient, which can remove such ribbons from the patient, and which can dispose of such ribbons, all without exposing therapy personnel to radiation hazards, and which can be detached from the ribbons during the therapy sessions so as to free up both the device and the patient.

SUMMARY

The afterloading device of the present invention satisfies this need. The invention is directed to a detachable and remote controllable afterloading device capable of transporting a plurality of ribbons comprising radioactive material into a plurality of conduits. The device comprises (a) a radiation-shielded container; (b) a plurality of channels within the container, each channel having a forward end and being adapted to transport the ribbons to and from the conduits; (c) a means for propelling the ribbons along the channels to and from the conduits such that at least a portion of the length of the ribbons is propelled into the conduits; and (d) at the forward end of the channels, a coupling element being detachable from the container, channels and propelling means.

The channels may be any substantially linear path capable of carrying the ribbons. Preferably, the channels are tubular conduits ("tubes").

The propelling means preferably comprises ring magnets which slide along the exterior of the channels, thereby causing a locally intense magnetic field to be induced within each channel. The ring magnets are mechanically linked to a power source which is adapted to move the ring magnets in unison back and forth within the shielded container.

In the embodiment of the invention comprising ring magnets, the coupling device is preferably a coupling-slide comprising (a) a first plate adapted to define a plurality of openings in the plane of such first plate; (b) a second plate affixed to the first plate in a plane parallel to the first plate and adapted to define a plurality of openings in the plane of such second plate; (c) a sliding plate affixed between the first and second plates such that the sliding plate is slideable within the plane of the sliding plate between a first sliding plate position and a second sliding plate position; and (d) a means for automatically sliding the sliding plate from the first sliding plate position to the second sliding plate position. A first opening in each of the first and second plates defines a first substantially straight line, and a second opening in each of the first and second plates defines a second substantially straight line. Also, the sliding plate is adapted so that when it is in the first sliding plate position, a first opening in the sliding plate is aligned along the first substantially straight line, and a second opening in the sliding plate is aligned along the second substantially straight line. The sliding plate is further adapted so that when it is in the second sliding plate position, the first opening in the sliding plate is not aligned with the first substantially straight line and the second opening in the sliding plate is not aligned with the second substantially straight line. Thus, when the sliding plate is in the first sliding plate position, ribbons can be passed through the three plates along the first and second substantially straight lines. Furthermore, if ribbons are stationary along the first and second substantially straight lines, attempting to shift the sliding plate to the second sliding plate position brings a clamping pressure to bear on the ribbons, thereby tending to hold the ribbons fast.

The invention is also directed to a ribbon article for administering radiation therapy comprising a substantially cylindrical elongated body wherein the body comprises radioactive material within the body and a non-radioactive, ferromagnetic material within the body so that the article can be remotely propelled along a conduit toward a patient by a device that utilizes in its propelling mechanism the magnetic attraction of the propelling device to the non-radioactive ferromagnetic material of the article.

DRAWINGS

These and other features, aspects and advantages of the present invention will become better understood with reference to the following description, appended claims and accompanying drawings where:

FIG. 6 is a partial cross-section of the shielded container shown in FIG. 1 illustrating optional shielded container and ribbon configurations adapted with a rear side clamping mechanism. FIG. 6B illustrates the clamping mechanism in the "unclamp" position, and FIG. 6C illustrates the clamping mechanism in the "clamp" position.

DESCRIPTION

The present invention is directed to a device for handling radioactive material used in connection with the irradiation of malignant tumors.

With reference to the figures, a handling or afterloading device embodying features of the invention comprises a radiation-shielded container 40 and a coupling-slide 41.

The shielded container 40 comprises an outer cylinder 1 and an inner cylinder 2 arranged coaxially along their central axes 46 and connected at their front ends (the left ends on FIG. 1) by a front plate 10 and at their rear ends (the right ends on FIG. 1) by a rear plate 11. The outer cylinder 1 and the inner cylinder 2 can be two sections of differing diameter pipe, fitted coaxially, one inside the other. For additional rigidity, an optional baffle 43 can be affixed at right angles to the central axis 46 between the outer cylinder 1 and the inner cylinder 2 at a location approximately midway between the front plate 10 and the rear plate 11. The outer cylinder 1 is affixed to the outer edge of the baffle 43, and the inner cylinder 2 is affixed to the inner edge of the baffle 43.

Figure 1:
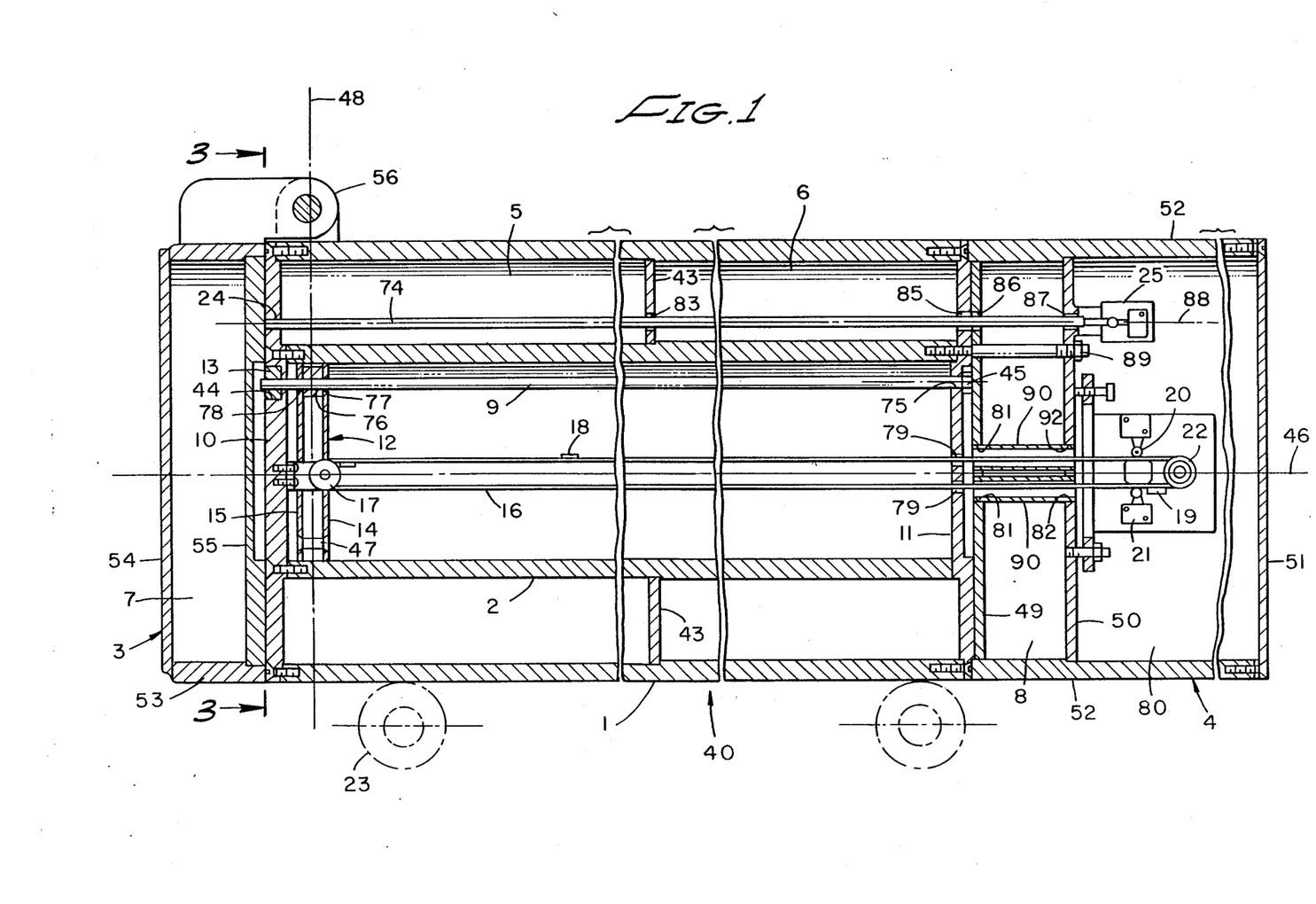
FIG. 1 is a longitudinal cross-section of the radiation-shielded container.

The front plate 10 is perforated with one or more front plate inner holes 44. One or more ribbon-holding tubes 9 are positioned within the inner cylinder 2 parallel to the central axis 46 and affixed at the front end to the front plate 10 and at the rear end to the rear plate 11. The inside diameters of the ribbon-holding tubes 9 are larger than the outside diameters of the ribbons 42 (described below). The number of ribbon-holding tubes 9 is the same as the number of front plate inner holes 44. Preferably, for the convenience of uniformity, the front plate inner holes 44 are of equal diameter, as are the ribbon-holding tubes 9. Each ribbon-holding tube 9 is aligned with corresponding front plate inner hole 44 such that each ribbon-holding tube 9 is open at the front end via a corresponding front plate inner hole 44 in the front plate 10. The outside diameter of each ribbon-holding tube 9 is the same as the inside diameter of its corresponding front plate inner hole 44 so that each ribbon-holding tube 9 fits tightly within its corresponding front plate inner hole 44. Optionally, the rear plate 11 is perforated with rear plate inner holes 75 in the same way as is the front plate 10. The number of rear plate inner holes 75 is no greater than the number of the ribbon-holding tubes 9. The rear plate inner holes 75 are spatially located such that each rear plate inner hole 75 is aligned with a corresponding ribbon-holding tube 9. The inside diameter of each rear plate inner hole 75 is the same as the outside diameter of its corresponding ribbon-holding tube 9 so that each ribbon-holding tube 9, when it is affixed to rear plate 11 at a corresponding rear plate inner hole 75, fits tightly within such corresponding rear plate inner hole 75. Affixing the rear end of a ribbon-holding tube 9 in alignment with a rear plate inner hole 75 causes that ribbon-holding tube 9 to be open-ended at its rear end. This is preferably the case with respect to all ribbon-holding tubes 9 for cleaning and maintenance purposes. Each ribbon-holding tube 9 which would otherwise be open-ended via a rear plate inner hole 75 is normally capped by a removable plug 45 that seals a rear plate inner hole 75 from the exterior of the inner cylinder 2.

A movable ring magnet 12, preferably a permanent magnet and preferably made from a samarium-cobalt material, is slideably attached to each ribbon-holding tube 9 by placing a ribbon-holding tube 9 inside the movable magnet central opening 76 of the movable magnet 12. The diameter of the movable magnet central opening 76 is slightly larger than the outside diameter of the corresponding ribbon-holding tube 9 so that such movable magnet 12 can easily slide along the exterior of such ribbon-holding tube 9, preferably without the necessity of lubrication.

All of the movable magnets 12 are aligned so that at any point in time they are always located in the same magnet plane 48, which plane is perpendicular to the central axis 46. The movable magnets 12 are maintained within the magnet plane 48 by the rear magnet positioning plate 14 and the front magnet positioning plate 15. The rear magnet positioning plate 14 is perforated with rear magnet positioning plate holes 77, and the front magnet positioning plate 15 is perforated with front magnet positioning plate holes 78. The number of the rear magnet positioning plate holes 77 and the number of front magnet positioning plate holes 78 are at least as many as the number of ribbon-holding tubes 9. The rear magnet positioning plate holes 77 and the front magnet positioning plate holes 78 are sized and spatially located such that when the rear magnet positioning plate 14 and the front magnet positioning plate 15 are aligned in planes perpendicular to the central axis 46 within the inner cylinder 2, each of the ribbon-holding tubes 9 protrudes through a corresponding rear magnet positioning plate hole 77 and a corresponding front magnet positioning plate hole 78 without touching either the rear magnet positioning plate 14 or the front magnet positioning plate 15. The front magnet positioning plate 15 is located within the inner cylinder 2 in a plane perpendicular to the central axis 46 and on the front side of the movable magnets 12. The rear magnet positioning plate 14 is located within the inner cylinder 2 in a plane perpendicular to the central axis 46 on the rear side of the movable magnet 12. The rear magnet positioning plate 14 and the front magnet positioning plate 15 are affixed to one another by a plurality of spacer pins 47 such that the distance between the rear magnet positioning plate 14 and the front magnet positioning plate 15 is only slightly larger the thickness of the movable magnets 12. Thus, as shown in FIG. 1, all of the movable magnets 12 are "sandwiched" between the rear magnet positioning plate 14 and the front magnet positioning plate 15 along the magnet plane 48.

The rear magnet positioning plate 14 and/or the front magnet positioning plate 15 are affixed within the inner cylinder 2 by attachment to a drive belt 16. The drive belt 16 is attached to a pulley 17 and a drive gear 22 such that the rotation of the pulley 17 and the drive gear 22 along their respective central axes will cause the drive belt 16 to rotate about the pulley 17 and the drive gear 22 in a manner similar to that of an automobile fan belt. The pulley 17 and the drive gear 22 are affixed within the shielded container 40 along a line parallel to the central axis 46 such that their respective central axes are parallel to one another and perpendicular to the central axes 46. The pulley 17 is affixed near the front end of the inner cylinder 2 such that when the drive belt 16 is rotated counter-clockwise with respect to the view shown in FIG. 1, the front magnet positioning plate 15 is caused to travel to a position within the inner cylinder 2 which is immediately adjacent to the front plate 10. The drive gear 22 is located to the rear of the rear plate 11. As shown in FIG. 1, two drive belt openings 79 in the rear plate 11 permit the drive belt 16 to travel into and out of the inner cylinder 2 between the pulley 17 and the drive gear 22. The drive gear 22 is caused to rotate about irs central axis by a power source (not shown), such as a small electric motor. The drive belt 16 can be a teethed belt, a chain, or any other suitable equipment capable of acting as a continuous drive belt.

Preferably, a first dog 18 and a second dog 19 are affixed within the shielded container 40 along the drive belt 16 such that they contact the rear end limit switch 20 and the front end limit switch 21 as the rear magnet positioning plate 14 approaches the rear plate 11 and as the front magnet positioning plate 15 approaches the front plate 10, respectively. The limit switches 20 and 21, which are affixed to the shielded container 40 such that their respective switching mechanisms are activated and deactivated by the dogs 18 and 19, are electrically connected to the power source which drives the drive gear 22 and are adapted to "switch off" the power source driving the drive gear 22 as the front magnet positioning plate 15 approaches the front plate 10 and as the rear magnet positioning plate 14 approaches the rear plate 11, respectively. When properly aligned, the interaction of the dogs 18 and 19 with the limit switches 20 and 21, respectively, act as automatic stopping devices for the magnet positioning plates 14 and 15. As shown in FIG. 1, the front magnet positioning plate 15 is proximate to the front plate 10. Thus, the second dog 19 is in contact with the front end limit switch 21. In this position, the front end limit switch 21 prevents any additional motion of the front magnet positioning plate 15 in the direction of the front plate 10. In similar fashion, as the rear magnet positioning plate 14 approaches the rear plate 11, the first dog 18 comes into contact with the rear end limit switch 20, which in turn deactivates the power source driving the drive gear 22, so as to prevent the rear magnet positioning plate 14 from contacting the rear plate 11.

Thus it can be seen that by engaging the drive gear 22, the drive belt 16 is caused to rotate in one direction or the other, thereby pulling the rear magnet positioning plate 14 and the front magnet positioning plate 15 in a direction parallel to the central axis 46. As the rear magnet positioning plate 14 and front magnet positioning plate 15 are moved back and forth along the central axis 46, they "drag" the movable magnets 12 back and front along with them. By this method, the movable magnets 12 are caused to slide from one end to the other along the exterior of the needle-holding tubes 9. The speed at which the drive gear 22 is rotated is typically adjustable depending upon the time required to load and unload the ribbons 42. The linear motion of the rear magnet positioning plate 14 and front magnet positioning plate 15 can be achieved using ball-slide spindles on any other mechanism capable of imparting motion in a direction parallel to the central axis 46.

To protect individuals from radioactivity, the drive gear 22 and the limit switches 20 and 21 are affixed to the shielded container 40 within a rear cover 4. The rear cover 4 is formed by a rear cover cylindrical section 52, a rear cover front plate 49 and a rear cover end plate 51. The rear cover cylindrical section 52 is substantially identical in cross section to the outer cylinder 1. The rear cover front plate 49 and the rear cover end plate 51 are also shaped substantially identically to the cross section of the outer cylinder 1. The rear cover front plate 49 and the rear cover end plate 51 are affixed to the rear cover cylindrical section 52 so as to define a rear cover vapor-tight chamber 80. The rear cover end plate 51 is attached to the rear cover cylindrical section 52 such that the rear cover end plate 51 can easily be removed to gain access to the rear cover vapor-tight chamber 80. The rear cover 4 is affixed to the outer cylinder 1 such that the rear plate 11 and the rear cover front plate 49 abut one another. A rear cover middle plate 50 is affixed in a plane parallel to the rear cover front plate 49 and is attached to the rear cover cylindrical section 52 between the rear cover front plate 49 and the rear cover end plate 51 so as to define a vapor-tight chamber 8. As shown in FIG. 1, the rear cover plate 49 is perforated with two rear cover front plate holes 81. Rear cover middle plate 50 is perforated with two rear cover middle plate holes 82. Each of the rear cover front plate holes 81 is located along a line parallel to the central axis 46 in direct alignment with a rear cover middle plate hole 82 and with a drive belt opening 79, such that the drive belt 16 is rotatable through the rear plate 11, the rear cover front plate 49 and the rear cover middle plate 50 without contacting any of the three plates. Two belt enclosing tubes 90 are affixed between the rear cover front plate 49 and the rear cover middle plate 50 such that they are in alignment with the two parallel paths of the drive belt 16 between the rear cover front plate 49 and the rear cover middle plate 50 and so as to form two "tunnels" between the rear cover front plate 49 and the rear cover middle plate 50. By this configuration, the drive belt 16 freely rotates without disturbing the integrity of the vapor-tight chamber 8. The rear cover 4 is attached to the inner cylinder 2 with bolts 89.

The front end of the shielded container 40 is normally covered by a front cover 3 which is formed by a front cover cylindrical section 53, a front cover first plate 54 and a front cover second plate 55. The front cover cylindrical section 53 has substantially the same cross-sectional shape as that of the outer cylinder 1. The front cover first plate 54 and the front cover second plate 55 also have substantially the same shape as the cross-section of the outer cylinder 1. The front cover first plate 54 and the front cover second plate 55 are attached to the front cover cylindrical section 53 in such a way as to form a vapor-tight front cover space 7. The front cover 3 is attached to the outer cylinder 1 such that the front cover second plate 55 and the front plate 10 abut one another. Preferably, the front cover 3 is conveniently swung away from the front plate 10 using a hinge mechanism 56 which is attached on one side to the outer cylinder 1 and on the other side to the front cover 3.

As can be seen in FIG. 1, the various plates and cylinders which comprise the shielded container 40 define several "empty spaces." These empty spaces can be packed with radioactivity-insulating material such as lead granulate. Thus, lead granulate or some other radioactivity-insulating material is normally packed within a first void space 5 which is defined by the outer cylinder 1, the inner cylinder 2, the front plate 10 and the baffle 43; a second void space 6 which is defined by the outer cylinder 1, the inner cylinder 2, the rear plate 11 and the baffle 43; the front cover space 7; and the vapor-tight chamber 8. It should be recognized, however, that the purpose of defining the first void space 5, the second void space 6, the front cover space 7 and the vapor-tight chamber 8 is solely for the purpose of providing a radioactivity-insulating "envelope" surrounding radioactive materials located within the ribbon-holding tubes 9. It should be appreciated that if such radioactive materials were small and/or if the inner cylinder 2, the front cover second plate 55 and the rear cover front plate 49 were sufficiently thick so as to provide adequate radioactivity-insulation by themselves, additional radioactivity-insulation would not be required and, therefore, the first void space 5, the second void space 6, the front cover space 7 and vapor-tight chamber 8 may not be required.

The baffle 43 is adapted with baffle holes 83, the plate 10 is adapted with front plate outer holes 24, the rear plate 11 is adapted with rear plate outer holes 85, the rear cover front plate is adapted with rear cover front plate holes 86, and the rear cover middle plate is adapted with rear cover middle plate holes 87. The baffle holes 83, the front plate outer holes 24, the rear plate outer holes 85, the rear cover front plate holes 86 and the rear cover middle plate holes 87 are aligned along one or more radial axes 88. The radial axes 88 are parallel to the central axis 46 and are located exterior to the inner cylinder 2. At least one linking rod 74, having a slightly smaller diameter than that of the baffle holes 83, the front plate outer holes 24 the rear plate outer holes 85, the rear cover front plate holes 86, and the rear cover middle plate holes 87, is slideably affixed to the shielded container 40 along each of the radial axes 88. The linking rods 74 are affixed within the shielded container 40 so that they are free to slide back and forth along the radial axes 88. The rear end of each of the linking rods 74 is proximate to an alignment confirming switch 25. Each of the alignment confirming switches 25 is affixed within the rear cover 4 and is adapted to disengage the power source driving the drive gear 22 unless the alignment confirming switch is in contact with a linking rod 74. The front end of each of the linking rods 74 terminates within one of the front plate outer holes 24.

Preferably, the needle-holding tubes 9 are constructed of a non-ferromagnetic material to minimize their magnetic interaction with the ribbons 42. Also, to minimize undesirable interference with the magnetic fields generated by the movable magnets 12 and the fixed magnets 13, it is preferable that the outer cylinder 1, the inner cylinder 2, the front plate 10, the rear plate 11, the rear magnetic positioning plate 14 and the front magnet positioning plate 15 be constructed of non-ferromagnetic material. To reduce undesirable magnetic field interference to the greatest extent possible, it is most preferable that all major components of the shielded container 40, except the movable magnets 12 and the fixed magnets 13, are constructed of non-ferromagnetic materials.

Preferably, the shielded container 40 is adapted with a plurality of casters 23 which are affixed to the external side of the outer cylinder 1 and adapted to allow the shielded container 40 to be easily moved along a horizontal surface. Optionally, the shielded container 40 can be housed in a movable cart (not shown) which also houses a control panel 109. Such a cart can be maneuvered in close proximity to the patient. The control panel 109 can comprise a portable remote control panel (not shown) which can be used to allow medical personnel to perform loading and unloading operations from a safe distance.

Figure 2A:
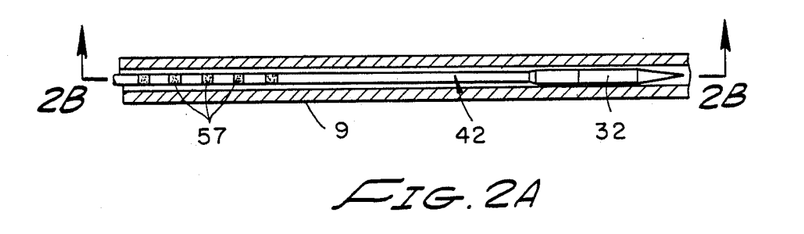
FIG. 2A is a longitudinal cross-section of an internal tube component of the shielded container of FIG. 1 showing a typical placement of a ribbon within that tube.
Figure 2B:
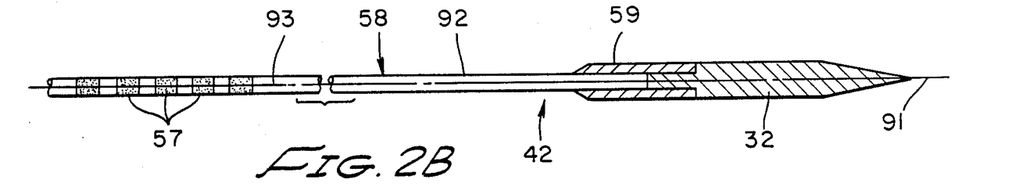
FIG. 2B is a longitudinal cross-section of another ribbon useful with the device of FIG. 1 taken along line 2B—2B in FIG. 2A.
Figure 3:
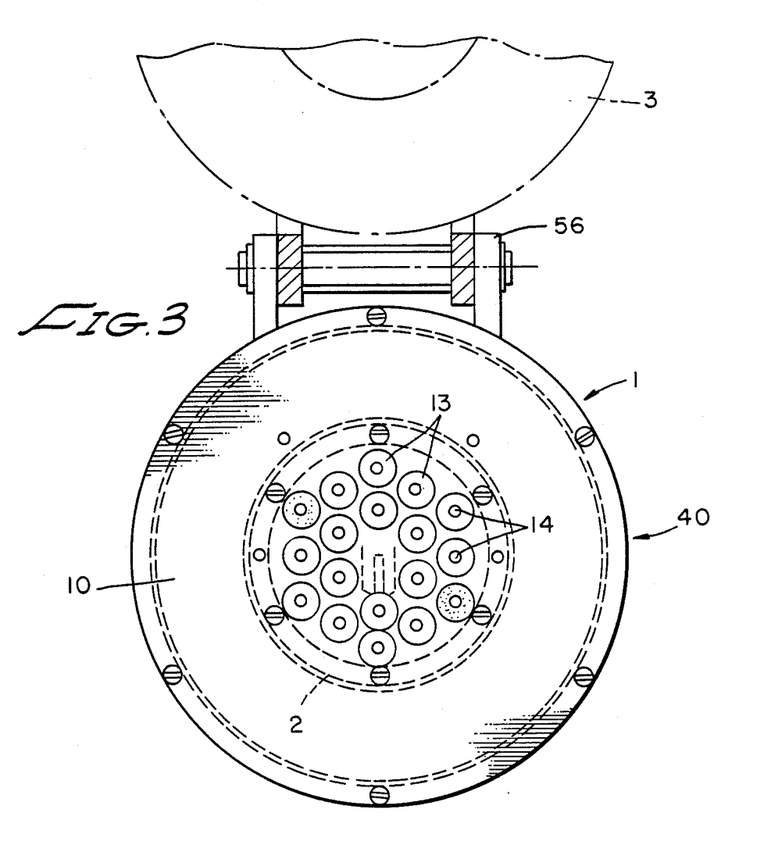
FIG. 3 is a front view of the shielded container of FIG. 1 taken along line 3—3 in FIG. 1.

The ribbon 42 is an elongated cylinder, usually having a length-to-circumference ratio greater than about 50:1. As used herein, the term "cylinder" is meant to indicate a solid bounded by two parallel planes and generated by a straight line moving parallel to the given planes and tracing a curve bounded by the planes and lying in a plane perpendicular to the given planes. The term "cylinder" is meant to include right circular cylinders, that is, cylinders having a circular cross-section. The ribbon 42 is comprised of a base piece 58, one or more radioactive seeds 57, and a ferromagnetic needle 32. The base piece 58 is composed of a flexible material such as a plastic. The seeds 57 are attached to the base piece 58, preferably, to give the afterloading device maximum range, at the end of the base piece 58. The ferromagnetic needle 32 is attached to the base piece 58, preferably, to maximize the afterloading device range, at the end of the base piece 58 opposite the end comprising the seeds 57. The needle axis of each needle 32 in substantially coincident with the axis of the base piece 58. The needle 32 is comprised of a ferromagnetic material, that is, a material such as iron which is easily magnetized and which is responsive to a weak magnetic field. The needle 32 has a sufficient mass that when a movable magnet 12 is slid along the exterior of a ribbon-holding tube 9, the ferromagnetic needle 32 is caused to "follow" the movable magnet 12 by sliding within the ribbon-holding tube 9. Preferably, the needle 32 is tapered to a point at its end farthest away from the seeds 57. Such tapering allows for the easy entry of the needles 32 into ribbon-holding tubes 9 having diameters only slightly larger than those of the ribbons 42.

Preferably, the ribbon 42 also comprises a leader member 59 which is affixed to the base piece 58 at a location along the central ribbon axis 93 between the radioactive seeds 57 and the needle 32. Preferably, for ease of removing and reinserting the needles 32, the leader member 59 is immediately adjacent to the needle 32, near the end of the ribbon 42 opposite the radioactive seeds 57. Also preferably, to protect the ribbon 42 from damage due to clamping forces, leader member 59 is composed of a non-ferromagnetic material which is harder than the material of which the base piece 58 is composed. For example, the leader member 59 can be composed of copper, brass or non-magnetic stainless steel. The leader member 59 allows for the clamping of the ribbon 42 near the end opposite the radioactive seeds 57 without damage to the ribbon 42. By making the leader member 59 of a non-ferromagnetic material, the leader member 59 does nor undesirably interact with the magnetic field generated by the movable magnets 12.

Each ribbon 42 has a cross-sectional shape similar to that of the cross-section of the ribbon-holding tubes 9 but of slightly smaller circumference. Preferably, the cross-sections of the ribbons 42 and the ribbon-holding tubes 9 are approximately circular with the diameter of the cross-section of the ribbons 42 being slightly smaller than the inside diameter of the cross-section of the ribbon-holding tubes 9. As so configured, a ribbon 42 is slid within a ribbon-holding tube 9 with limited force but does not tend to "bunch up."

It should be realized that the methods used to attach the four components of the ribbon 42 are not critical. It is also not critical that the ribbon 42 be of uniform shape and circumference along its length. It is sufficient that the differences in shape and circumference are small enough to allow the easy travel of the ribbon 42 within the ribbon-holding tube 9 without binding or "bunching up." An exemplary ribbon 42 contains five radioactive cesium seeds 57 embedded in one end of a nylon base piece 58; a needle 32 is composed of iron and is affixed to the base piece 58 at the end opposite the radioactive seeds 57; a leader member 59 is a thin brass cylinder which is affixed tightly to the exterior of the base piece 58 at a location between the radioactive seeds 57 and the needle 32 and is immediately adjacent to the needle 32; the overall length of the ribbon 42 is 815 millimeters and its outside diameter is about three millimeters; the ferromagnetic needle 32 is thirty-three millimeters long and about three millimeters outside diameter; and the leader member 59 is sixty-two millimeters long and about two millimeters outside diameter.

Figure 6A:
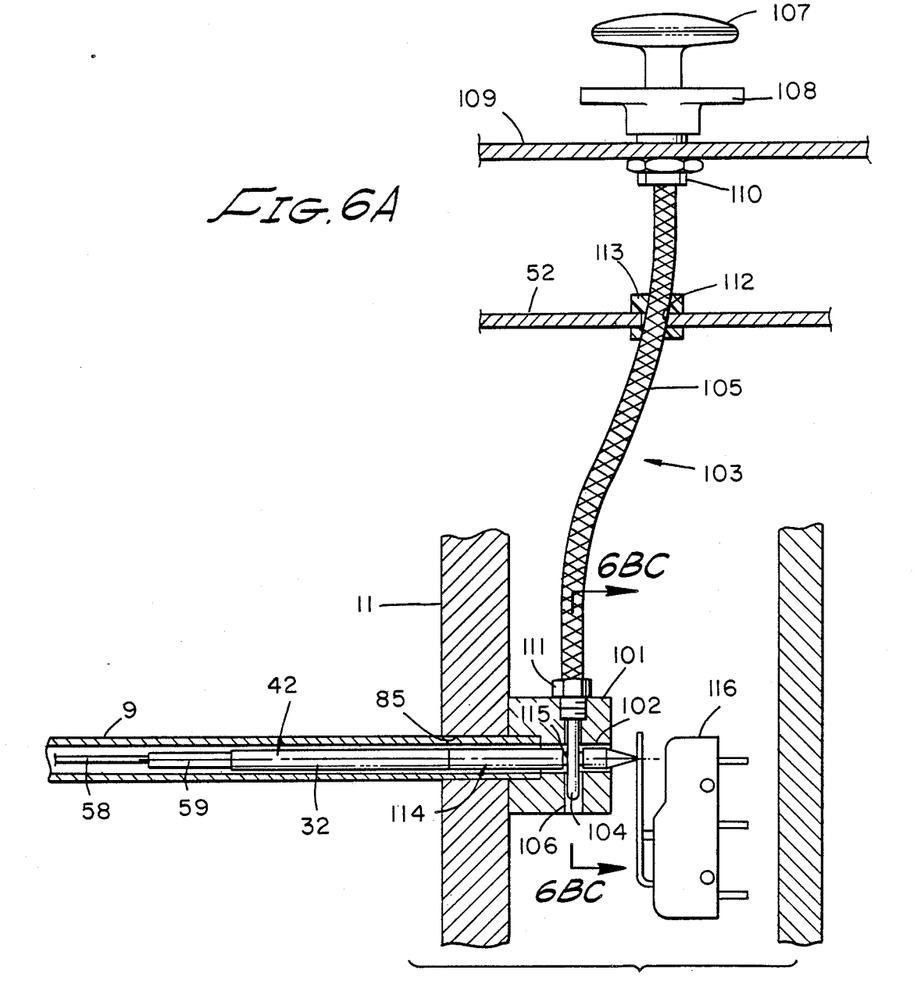
FIG. 6A is a partial longitudinal cross-section of the tubes and rear plate of the shielded container device shown in FIG. 1.
Figure 6B:
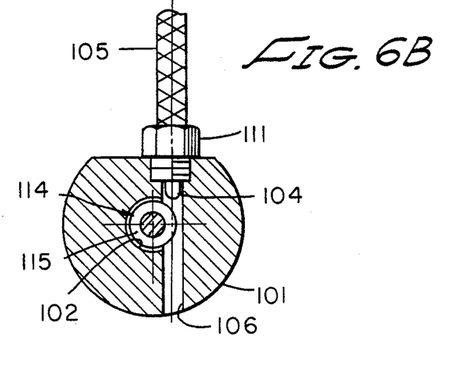
FIGS. 6B and 6C are radial cross-sections of the clamp housing shown in FIG. 6A taken along line 6BC—6BC.
Figure 6C:
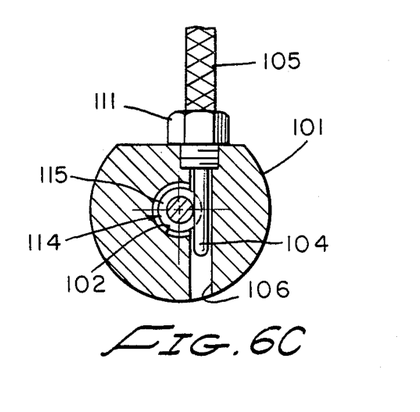

FIG. 6 illustrates optional configurations of the shielded container 40 and the ribbons 42 which allow the ribbons 42 to be locked within the tubes 9. In the optional configuration of the container 40, a clamp housing 101 is attached to the rearward side of the rear plate 11. The clamp housing 101 has a lateral bore 102 which is aligned with the rear plate outer hole 85 so that a ribbon 42 can be passed from the tube 9 through the clamp housing 101. The clamp housing 101 is adapted with a clamp mechanism 103 which is disposed within the clamp housing 101 in such a way that it can alternately clamp down upon and release a ribbon 42 disposed within the clamp housing 101. FIG. 6 illustrates one example of the clamp mechanism 103. In this example, the clamp mechanism 103 is a typical cable comprised of a cable 104 sheathed in a cable sheath 105. One end of the cable 104 is disposed within a cable bore 106 which is drilled at approximately right angles to the lateral bore 102 in such a way that the cable 106 and the lateral bore 102 cross but do not precisely coincide (see FIGS. 6B and 6C). The other end of the cable 104 is affixed to a handle 107 which is slideably disposed within a handle housing 108. As so disposed, the cable 104 can be slid within the sheath 105 by sliding the handle 107 within the handle housing 108. For convenience, it is preferable that the handle housing 108 be attached to the externally disposed control panel 109 by a first fastening mechanism 110. The sheath 105 is affixed to the clamp housing 101 by a second fastening mechanism 111. The sheath is sealed in a cable sheath opening 112 in the rear cover cylindrical section 52 by cable seal 113. In the optional configuration of the ribbon 42, a rear leader element 114 is affixed to the end of the needle 32 opposite the leader element 59. The rear leader element 114 is composed of a non-ferromagnetic material so that it is not attracted to the magnet 12. The rear leader element 114 is preferably pointed on the end opposite the needle 32 to facilitate insertion of the ribbon 42 into the tube 9. The rear leader element 114 is notched with a notch 115 which is adapted to receive the cable 104 as illustrated in FIGS. 6A and 6C. In operation, the ribbon 42 is clamped within the tube 9 by sliding the handle 107 within the handle housing 108 so as to withdraw the cable 104 from the lateral bore 102 of the clamp housing 101. The ribbon 42 is slid to the rear of the tube 9 by the magnets 12, thereby thrusting the rear leader member 114 into the lateral bore 102. The notch 115 is aligned with the cable bore 106. The handle 107 is slid within the handle housing 108 so as to thrust the cable 104 into the lateral bore 102, thereby engaging the notch 115. The notch 115 can be aligned within the cable bore 106 by the contact of the first dog 18 with the limit switch 20. Optionally, a clamp alignment limit switch 116 can be positioned to the rear of the clamp housing 101 in such a way that the rear leader element 114 sliding rearwardly within the tube 9 will impinge the limit switch 116 thereby disengaging the drive mechanism 22 at the moment that the notch 115 is aligned with the cable bore 106.

Figure 4:
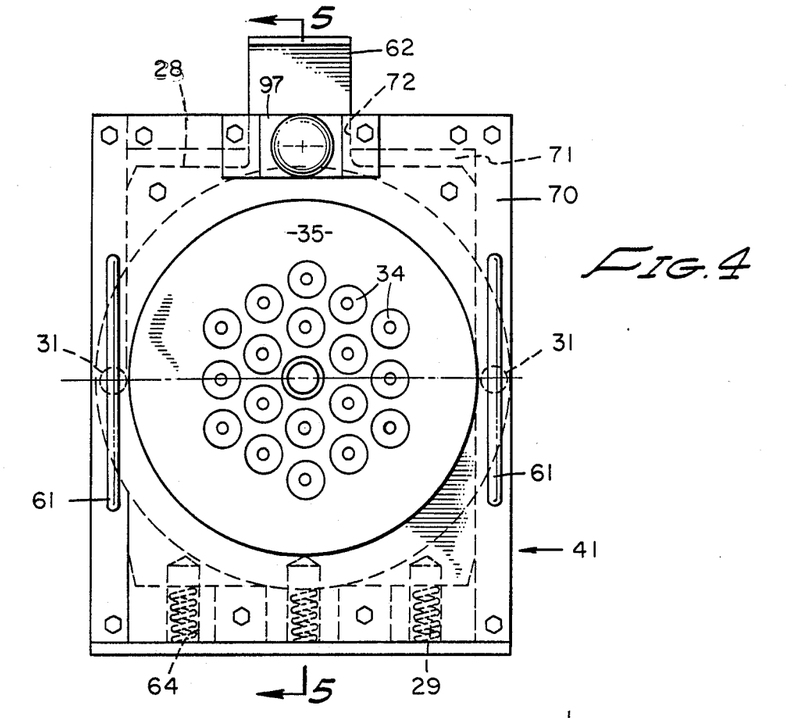
FIG. 4 is a front view of the coupling-slide.
Figure 5:
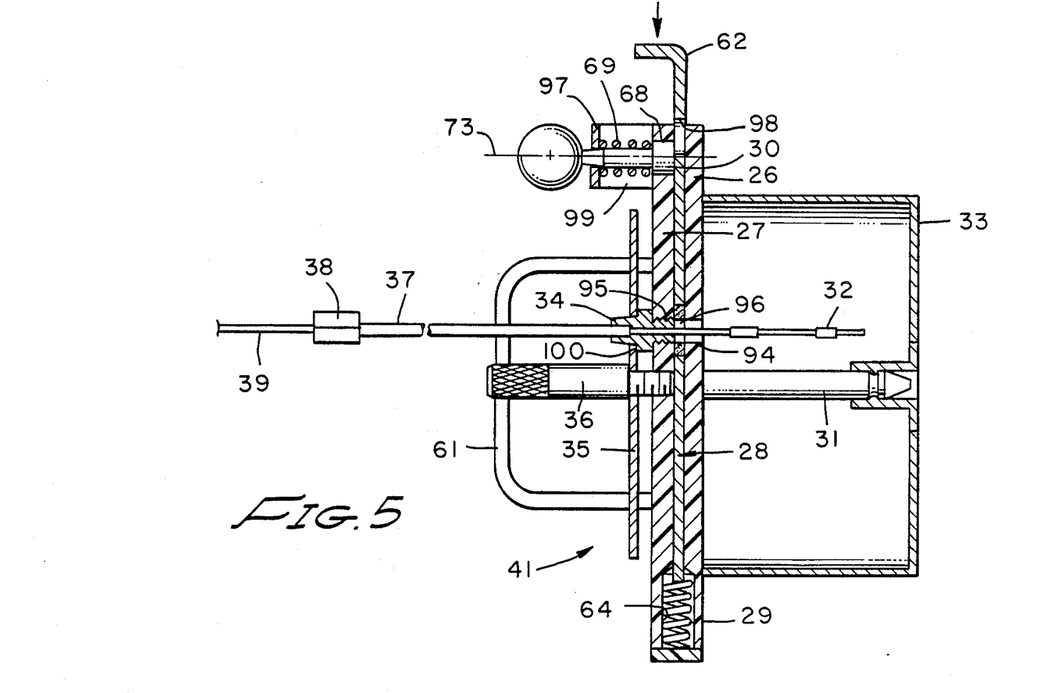
FIG. 5 is a cross-section of the coupling-slide of the device of FIG. 1 taken along line 4—4 in FIG. 4.

The coupling-slide 41 is a clamping mechanism which is used to clamp down upon all of the ribbons 42 simultaneously after the ribbons 42 have been transported out of the shielded container 40. The clamping force exerted on the ribbons 42 by the coupling-slide 41 is greater that the magnetic force exerted by the movable magnets 12 upon the needles 32. Since the ribbons 42 are only held within the shielded container 40 by the magnetic forces generated by the movable magnets 12, the ribbons 42 are easily removed from the shielded container 40. The coupling-slide 41 allows for the removal of the ribbons in an orderly manner and holds the ribbon tail ends, i.e. the needles 32, rigidly in a single configuration. Preferably, the needles 32 are each parallel to one another so that the ribbons 42 can be easily reinserted into the shielded container 40 upon completion of the therapy session. The coupling-slide 41 comprises a posterior plate 26 and an anterior plate 27, each composed of a light-weight, non-ferromagnetic material such as aluminum or plastic. One side of both plates is flat whereas the other side of both plates is slightly recessed below a border area 70 around their perimeters. The recessed areas of both plates are substantially identical in shape so that when the posterior plate 26 and anterior plate 27 are affixed together with the recessed spaces facing one another, they define a rectangular parallelepiped void space 71 created by the combined recessed areas of the two plates. A sliding plate 28 is affixed between the posterior plate 26 and the anterior plate 27 within the rectangular parallelepiped void space 71 such that the sliding plate 28 is slideably transpositionable therein. The sliding plate 28 has a slightly less thickness than the depth of the rectangular parallelepiped void space 71. A tab 62 is attached at the top of the sliding plate 28 and, when the sliding plate 28 is affixed in place between the posterior plate 26 and the anterior plate 27, protrudes through a gap 72 created by the recessing of like sections of the border 70, of posterior plate 26 and anterior plate 27. Thus, although most of the sliding plate 28 is encapsulated within the posterior plate 26 and the anterior plate 27, the sliding plate 28 can be made to slide up and down by manipulating the tab 62.

The posterior plate 26 is perforated with posterior plate holes 94. The anterior plate 27 is perforated with anterior plate holes 95. The sliding plate 28 is perforated with sliding plate holes 96. The configuration of the posterior plate holes 94, the anterior plate holes 95 and the sliding plate holes 96 is substantially identical to the configuration of the front plate holes 44, so that when the posterior plate 26 is caused to be abutted against the front plate 10, there is one hole in each of the posterior plate 26, the anterior plate 27 and the sliding plate 28 which can be made to align with a corresponding front plate inner hole 44. In this way, when the coupling-slide 41 is attached to the shielded container 40 such that the posterior plate 26 abuts the front plate 10, each of the front plate inner holes 44, the posterior plate holes 94, the anterior plate holes 95 and the sliding plate holes 96 can be aligned along an axis coincident with a central needle axis 91 such that a ribbon 42 within a ribbon-holding tube 9 can be extracted from the ribbon-holding tube 9 via a front plate inner hole 44, a posterior plate hole 94, an anterior plate hole 95 and a sliding plate hole 96.

The diameter of the posterior plate holes 94 and the anterior plate holes 95 are approximately the same size or, optionally, slightly larger than the front plate inner holes 44. The sliding plate holes 96 are preferably slightly larger than the front plate inner holes 44 to accommodate a ring of soft material, such as rubber, placed within the sliding plate holes 96 and yet defining an openings in each of the sliding plate holes 96 sufficiently large to allow ribbon 42 to travel through it.

The posterior plate 26 and the anterior plate 27 are also recessed in one or more abutting areas along the border 70 opposite the taco 62 so that when the posterior plate 26 and the anterior plate 27 are affixed together, one or more spring housing spaces 64 are defined which are capable of housing springs 29. The springs 29 are affixed within spring housing spaces 64 in such a way that they impinge the sliding plate 28, thereby exerting an upward force upon the sliding plate 28. Thus, it can be seen that, unless an external downward pressure is brought to bear on the tab 62, the sliding plate 28 will tend to remain at rest in the upward portion of the rectangular parallelepiped void space 71, elevated in this manner by the upward force exerted by the springs 29. The sliding plate holes 96 are so configured that they align with the posterior plate holes 94 and the anterior plate holes 95 when the sliding plate 28 is in its lower-most position within the rectangular parallelepiped void space 71, a position possible only by applying a counteracting force to the upward force exerted by the springs 29. An indexing pin 30, affixed to the anterior plate 27 by an indexing pin housing 97 and aligned such that a central indexing pin axis 73 is perpendicular to the anterior plate 27, can be used to lock the sliding plate 28 in its lower-most position by protruding through an anterior plate indexing pin opening 68 and a sliding plate indexing pin opening 98 in the sliding plate 28. An indexing pin spring 69 is affixed within an indexing pin spring housing 99 such that indexing pin spring 69 impinges on the indexing pin 30 in a manner tending to cause the indexing pin 30 to travel towards the sliding plate 28. Thus, when the sliding plate 28 is pushed downward such that the indexing pin 30 is aligned with the anterior plate indexing pin opening 68, the indexing pin spring 69 causes the indexing pin 30 to automatically travel into the anterior plate indexing pin opening 68, thereby automatically engaging the sliding plate 28.

The coupling-slide 41 is equipped with two or more locating pins 31 affixed to the coupling-slide 41 perpendicular to the posterior plate 27. The locating pins 31 assist in attaching the coupling-slide 41 to the shielded container 40 as described below. Preferably, the locating pins 31 are of differing diameter to insure that the coupling-slide 41 is attached to the shielded container 40 in one and only one position.

Connecting adapters 34, adapted to connect an anterior plate hole 95 in fluid-tight communication with an external tube 37 is affixed to the anterior plate 27 at each anterior plate hole 95. Optionally, a retainer plate 35, adapted with retainer plate holes 100 in substantially the same spatial configuration as the anterior plate holes 95 and having diameters larger than the exterior tubes 37 but smaller than the largest diameter of the connecting adapters 34 can be used to retain and affix the connecting adapters 34 to the anterior plate 27. A threaded pin 36 can be used to screw the retainer plate 35 to the anterior plate 27.

A coupling-slide cover 33 is detachably affixed to the posterior plate 26. The coupling-slide cover 33 is configured so that, when attached to the posterior plate 26, it will define a volume sufficient in location and size to encompass the rear ends of the ribbons 42 after the coupling-slide 41 has been used to clamp down upon the ribbons 42 and the coupling-slide 41 has been detached from the shielded container 40.

The coupling-slide 41 is also equipped with one or more handles 61 for ease in grasping the coupling-slide 41 during its removal from, and its attachment to, the shielded container 40. Preferably, the coupling-slide 41 is relatively light in weight, e.g. about 700 gm., so that during the therapy session it can be easily carried about by the therapy patient.

FIG. 5 shows a typical ribbon 42 which has been clamped by the coupling-slide 41. The ribbon 42 has been removed from the shielded container 40 and has been afterloaded into an interstitial or intercavitary conduit 39 via a flexible exterior tube 37. The exterior tube 37 is attached to the coupling-slide 41 by a connecting adapter 34 which, in turn, has been affixed to the posterior plate 27, such that a central opening within the connecting adapter 34 is in alignment with one of the holes in the anterior plate 27. As so aligned, the ribbon 42 is allowed to traverse the coupling-slide 41 through aligned holes in the posterior plate 26, the anterior plate 27 and the sliding plate 28, through the open area defined by the connecting adapter 34 and into the exterior tube 37. As shown in FIG. 4, the exterior tube 37 is attached to the interstitial or intercavitary conduit 39 via a conduit-tube connector 38.

In operation, the front cover 3 is opened on the shielded container 40 to reveal the open ends of the empty ribbon-holding tubes 9 through the front plate inner holes 44. Movable magnets 12 are positioned adjacent to the front plate 10 by the rear magnet positioning plate 14 and the front magnet positioning plate 15 which are driven by an external power source (not shown) that drives belt 16. The second dog 19 automatically trips the front end limit switch 21 when the movable magnets 12 are as close as possible to the front plate 10. The movable magnets 12 generate a locally intense magnetic field within that portion of the ribbon-holding tubes 9 which are surrounded by the movable magnets 12. A radiation-insulated shipping container containing the ribbons 42 is removed from storage and placed proximate to the front plate 10. Preferably the non-radioactive ferromagnetic needle 32 of each of the ribbons 42 is accessible outside of the radioactivity-insulated portion of the shipping container.

A technician places the ferromagnetic element of at least one of the ribbons 42 into a ribbon-holding tube 9. The locally intense magnetic field generated by the movable magnets 12 and the fixed magnets 13 causes the needles 32 to magnetically adhere to the shielded container 40 just inside the front plate inner holes 44. The technician then adjourns to a remote location and, by remote control such as by the use of an infrared remote control device, activates a power source which turns the drive gear 22. The drive gear 22, acting through the drive belt 16, slides the rear magnet positioning plate 14 and the front magnet positioning plate 15 towards the rear plate 11. In so doing, the front magnet positioning plate 15 tows the movable magnets 12 along with it. As the movable magnets 12 travel along the ribbon-holding tubes 9 the locally intense magnetic field generated within the ribbon-holding tubes 9 moves as well. Thus, as the movable magnets 12 are towed toward the rear plate 11, the ferromagnetic needles 32, because they are responsive to the locally intense magnetic field, are caused to move within the ribbon-holding tubes 9 in the direction of rear plate 11. As they travel, the needles 32 draw the remainder of the ribbons 42 into the ribbon-holding tubes 9. The rear magnet positioning plate 14 and the front magnet positioning plate 15 are retracted to a point as close as possible to the rear plate 11. When this position is achieved, the first dog 18 trips the rear end limit switch 20, which, in turn, disengages the power source turning the drive gear 22 and thus halts the movement of the rear magnet positioning plate 14 and the front magnet positioning plate 15. As the movable magnets 12 travel towards the rear plate 11 they draw with them the ribbons 42 out of the shipping container. The ribbons 42 are shorter than the ribbon-holding tubes 9 so that when the rear magnet positioning plate 14 and the front magnet positioning plate 15 are retracted proximate to the rear plate 11, the ribbons 42, including their radioactive seeds 57, are completely withdrawn into the ribbon-holding tubes 9.

After loading the ribbons into the container, the technician affixes the coupling-slide 41 to the shielded container 40 by placing the locating pins 31 into the front plate outer holes 24. The locating pins 31 push on the linking rods 70 to engage the alignment confirming switches 25. The tab 62 is depressed so that the posterior plate holes 94, the anterior plate holes 95 and the sliding plate holes 96 are aligned with a corresponding front plate inner hole 44. The indexing pin 30 is engaged into the anterior plate indexing pin opening 68 to hold the sliding plate holes 96 in alignment with the posterior plate holes 94 and the anterior plate holes 95.

The interstitial or intercavitary conduits 39 are connected to the coupling-slide 41 via the conduit-exterior tube connectors 38, the exterior tubes 37 and the connecting adapters 34. If there are less interstitial or intercavitary conduits 39 then there are ribbons 42 loaded within the shielded container 40, plugs (not shown) are inserted into those anterior plate holes 95 corresponding to the ribbon-holding tubes 9 containing excess ribbons 42.

The technician then activates the power source driving the drive gear 22. Such power source functions only if the alignment confirming switches 25 are in contact with the corresponding locating pins 31 within the front plate outer holes 24. Assuming this to be the case, the rear magnet positioning plate 14 and the front magnet positioning plate 15 slide toward the front plate 10, thereby towing with them movable magnets 12 in the direction of the forward plate 10. As the movable magnets 12 slide toward the forward plate 10, the locally intense magnetic field within the ribbon-holding tubes 9 travels with them. The ferromagnetic needles 32 of the ribbons 42, which are responsive to the locally intense magnetic field created by the movable magnets 12, are thus propelled within the ribbon-holding tubes 9 in the direction of the front plate 10. The movement of the ferromagnetic needles 32 pushes against the remainder of the ribbons 42 causing the ribbons 42 to brushed through the front plate holes 44, through the posterior plate holes 94, through the sliding plate holes 96, through the anterior plate holes 95, and into the interstitial or intercavitary conduits 39 via the exterior tubes 37. The travel of the ribbons is halted by disengaging the power source driving the drive gear 22. This can be accomplished by manually disengaging the power source, by the preprogrammed disengagement of the power source using a computerized controller, or by the automatic disengagement of the power source by the action of dog 18 tripping limit switch 20.

If the ribbons 42 are to be disconnected from the shielded container 40, the indexing pin 30 is retracted out of the sliding plate 28. The springs 29 press upward against the sliding plate 28 causing the sliding plate 28 to attempt to travel in an upward direction away from the springs 29. The upward pressure exerted by the springs 29 causes the soft material within the sliding plate holes 96 to impinge the ribbons 42 at their respective leader members 59, thereby clamping the ribbons 42 and holding them rigidly in position. The coupling-slide 41 is then removed from the shielded container 40 by grasping the handles 61 and pulling the locating pins 31 out of the front plate outer holes 24. Because the ferromagnetic needles 32 of the ribbons 42 are only held within the ribbon-holding tubes 9 by the magnetic field generated by the movable magnets 12 and the fixed magnets 13, the ribbons 42 are easily detached from the shielded container 40.

After the coupling-slide 41 has been detached from the shielded container 40, the ferromagnetic needles 32 of the ribbons 42 and the locating pins 31 are covered by the coupling-slide cover 33. The coupling-slide 41, because it is relatively small and light, can be attached to the patient's person with a strap or belt, thereby allowing the patient to move about.

When radiation therapy is complete, the coupling-slide cover 33 is removed from the coupling-slide 41 and the coupling-slide 41 is reattached to the shielded container 40. Because the tail ends of the ribbons 42 are rigid, and because the coupling-slide 41 holds such rigid ends firmly in place, the tail ends of the ribbons 42 continue to remain in precise alignment within the front plate inner holes 44, allowing easy re-insertion of the ribbons 42 into the ribbon-holding tubes 9. In so doing, the locating pins 31 press against the linking rods 74 which engage the alignment confirming switches 25, allowing the power source driving the drive gear 22 to operate. The rear magnet positioning plate 14 and the front magnet positioning plate 15, which have been stationary during the reattachment of the coupling-slide 41 at the position closest to the front plate 10, are then retracted towards the rear plate 11 by the movement of the drive belt 16. As the rear magnet positioning plate 14 and the front magnet positioning plate 15 retract, the movable magnets 12 retract with them, thereby pulling the ribbons 42 out of the interstitial or intercavitary conduits 39, through external tubes 37 and back into the ribbon-holding tubes 9.

To dispose of the used ribbons 42 after being retracted back into the ribbon-holding tubes 9, the technician can detach the external tubes 37 from the coupling-slide 41 and attach, in their place, one or more tubes or conduits which terminate within a radiation-insulated storage container. The technician then engages the power source which drives the drive gear 22 to push the used ribbons 42 out of the ribbon-holding tubes 9, through the newly-attached disposal tube or conduits and into the radioactivity-insulated storage container.

Although the present invention has been described in considerable detail with regard to various versions thereof, other versions are possible. For example, the movable magnets 12 need not be ring-shaped. Other geometric shapes can also be functional in the invention so long as they can generate a movable, locally intense magnetic field within the ribbon-holding tubes 9. Nor do the movable magnets 12 need be permanent magnets. Electromagnets can be substituted. Furthermore, the invention is not restricted to embodiments wherein the electromagnetic field is generated by the movable magnets 12. If the needles 32 were themselves magnetized, then the invention would be operable in substantially the same way using non-magnetized elements in place of the movable magnets 12, so long as the non-magnetized elements were composed of a ferromagnetic material.

The afterloading device of the invention has many significant advantages compared to devices of the prior art. It allows for the automatic afterloading of the radioactive material into a therapy patient, thereby protecting therapy personal from the hazards of radiation exposure, and still allows the patient to be "detached" from the automatic afterloading device. The device of the invention also allows the re-attachment to the radioactive material-carrying ribbons so that the ribbons can be automatically removed from the patient, stored within the shielded container, and later reused or transferred to a shielded disposal vessel, all without exposing therapy personnel to radiation hazards.

What is claimed is:

1. An afterloading device for inserting a ribbon containing radioactive material into a thin, hollow conduit which has been placed within or adjacent to a tumor of a medical patient, wherein the ribbon has a first end composed of a non-ferromagnetic material and a second end comprising a ferromagnetic material and wherein the thin, hollow conduit has a first end placed within or adjacent to the tumor and an open second end which is accessible outside of the patient's body, the afterloading device comprising:
    (a) a radiation-shielded container;
    (b) at least one non-ferromagnetic tube within the container, the tube having a first end, an open second end, a longitudinal axis, an exterior surface and an interior surface;
    (c) a magnet disposed within the container proximate to the exterior surface of the tube;
    (d) means for moving the magnet proximate to and in parallel with the exterior surface of the tube between a first magnet position located proximate to the first end of the tube and a second magnet position located proximate to the second end of the tube; and
    (e) connection means for connecting the second end of the thin, hollow conduit in communication with the second end of the tube;
so that when the ribbon is within the tube with the second end of the ribbon proximate to the first end of the tube and when the magnet is at the first magnet position and when the second end of the conduit is connected in communication with the open second end of the tube, the first end of the ribbon can be slid from the tube into the conduit by causing the magnet to slide from the second magnet position to the first magnet position.

2. The device of claim 1 wherein the connection means is a coupling-slide comprising:
    (a) an anterior plate defining at least one anterior plate hole capable of receiving the ribbon;
    (b) a posterior plate attached rigidly in parallel to the anterior plate; the posterior plate defining a posterior plate hole capable of receiving the ribbon and aligned with the anterior plate hole such that a straight line disposed normal to the anterior and posterior plates pass through the centers of the anterior plate hole and the posterior plate hole;
    (c) a sliding plate disposed between, proximate to and in parallel with the anterior plate and the posterior plate, the sliding plate defining a sliding plate hole capable of receiving the ribbon; and
    (d) means for sliding the sliding plate between a first sliding plate position wherein the straight line disposed normal to the anterior and posterior plates and passing through the centers of the anterior and posterior plate holes also passes through the center of the sliding plate hole, and a second sliding plate position wherein the line normal to the anterior and posterior plates and passing through the centers of the anterior and posterior plate holes does not pass through the center of the sliding plate hole.

3. The device of claim 2 wherein the means for sliding the sliding plate comprises a spring which is disposed between the anterior plate and the posterior plate to impinge upon the sliding plate and urge the sliding plate from the first sliding plate position to the second sliding plate position.

4. The device of claim 2 further comprising a locking pin having a longitudinal axis disposed proximate and normal to the anterior plate and wherein the anterior plate and the sliding plate each define an opening capable of receiving the locking pin and wherein the opening defined in the sliding plate is aligned with the opening defined in the anterior plate such that a straight line coincident with the longitudinal axis of the pin passes through the center of the openings defined in the sliding plate and in the anterior plate when the sliding plate is in the first sliding plate position.

5. The device of claim 2 further comprising a removable plug disposed within the hole defined in the anterior plate.

6. The device of claim 2 further comprising a connecting adapter; the connecting adapter defining a bore having a first bore end, a second bore end and a longitudinal axis, the first bore end being adapted to receive the second end of the thin, hollow conduit and the second bore end being disposed within the hole defined in the anterior plate such that the second bore opening is in communication with the hole in the posterior plate when the sliding plate is in the first sliding plate position.

7. The device of claim 1 comprising a plurality of tubes and wherein the magnets are ring magnets.

8. The device of claim 7 wherein the number of holes defined in the posterior plate is the same as the number of tubes.

9. The device of claim 1 wherein the means for moving the magnets comprises:
  (a) a magnet positioning plate disposed within the container and normal to the tube, the positioning plate defining a positioning plate hole capable of receiving the tube and through which the tube is disposed, the positioning plate hole being incapable of coincidentally receiving the magnet; and
  (b) means for moving the positioning plate between a first positioning plate location located proximate to the first end of the tube and a second positioning plate location located proximate to the second end of the tube; such that when the positioning plate is moved from the first positioning plate location to the second positioning plate location, the magnet is moved from the first magnet position to the second magnet position.

10. The device of claim 1 further comprising a means for locking the ribbon within the tube.

11. The device of claim 10 wherein the first end of the tube is open and wherein the means for locking the ribbon comprises:

(a) a clamp housing disposed within the shielded container, proximate to the first end of the tube; the clamp housing defining a lateral bore having a longitudinal axis which is in communication with, and aligned with, the open first end of the tube such that the longitudinal axis of the lateral bore and the longitudinal axis of the tube lie along the same straight line; the clamp housing further comprising a second bore which intersects and communicates with the lateral bore;
  (c) a cable disposed within the second bore in such a way that it intrudes into the lateral bore and impinges, and thereby locks, the second end of the ribbon when the second end of the ribbon is disposed within the lateral bore; and
  (d) retracting means for moving the cable within the second bore from a first cable position wherein the cable intrudes into the lateral bore and impinges upon the second end of a ribbon disposed within the lateral bore, and a second cable position wherein the cable does not intrude into the lateral bore.

12. A method for inserting a ribbon containing radioactive material into a thin, hollow conduit having a first end and an open second end, wherein the ribbon has a first end composed of a non-ferromagnetic material and a second end comprising a ferromagnetic material and wherein the thin, hollow conduit has a first end and an open second end, the method comprising:
  (a) inserting the ribbon into a non-ferromagnetic tube having a first tube end and an open second tube end; the tube being disposed within a radiation-shielded container; the ribbon being inserted into the tube such that the second end of the ribbon is proximate the first end of the tube;
  (b) connecting the open second end of the thin, hollow conduit in communication with the open second end of the tube;
  (c) inducing the first end of the ribbon to move from the tube into the thin, hollow conduit by sliding a magnet along the exterior surface of the tube from a starting position located proximate to the first end of the tube to an ending position located proximate to the second end of the tube; and
  (d) clamping the ribbon at a location on the ribbon which is exterior of the tube and removing from the tube any portion of the ribbon remaining with the tube.

* * * * *